United States Patent [19]

Patel

[11] 4,266,086

[45] May 5, 1981

[54] PROCESS FOR REMOVING α-ACETYLENES FROM DIOLEFINS

[75] Inventor: Pradeep V. Patel, Parma, Ohio

[73] Assignee: The B. F. Goodrich Company, Akron, Ohio

[21] Appl. No.: 120,948

[22] Filed: Feb. 12, 1980

[51] Int. Cl.$^3$ .............................................. C07C 7/177
[52] U.S. Cl. ................................... 585/810; 585/834; 585/843; 585/845; 585/847; 585/837; 585/852
[58] Field of Search .............. 585/259, 843, 906, 810, 585/834, 845, 847, 852, 848, 850

[56] References Cited

U.S. PATENT DOCUMENTS

| | | | |
|---|---|---|---|
| 2,398,301 | 4/1946 | Frevel | 585/848 |
| 2,408,970 | 10/1946 | Doumani et al. | 585/848 |
| 2,953,608 | 9/1960 | Fernald | 585/848 |
| 3,105,858 | 10/1963 | Kresge et al. | 585/906 |
| 4,064,190 | 12/1977 | Eastman et al. | 585/848 |
| 4,174,355 | 11/1979 | Patel et al. | 585/843 |

*Primary Examiner*—Veronica O'Keefe
*Attorney, Agent, or Firm*—Alfred D. Lobo; J. Hughes Powell, Jr.

[57] ABSTRACT

Conjugated diolefins contaminated with relatively high levels of acetylenic impurities in a hydrocarbon feedstream are purified by a cyclic, liquid phase, predominantly catalytic cracking process which selectively removes alpha-acetylenes in a single pass. The energy requirement for removing the alpha-acetylenes in this liquid phase process are from about one-third to about one-fifth as great as that required in a comparable vapor phase process. A feedstream containing about equal weights of butadiene and mixed monoolefins and alkanes contaminated with alpha-acetylenes including vinyl acetylene and methyl acetylene, inter alia, in an amount up to about 1.0 percent by weight (% by wt) of the feedstream, is contacted in the liquid phase with a supported Group I B metal oxide catalyst in the absence of hydrogen, at a temperature in the range from about 200° F. to about 260° F. Despite the relatively high temperature range at which butadiene monomer is contacted with the catalyst for a relatively long time, the loss of diolefin due to polymerization is less than 1% by wt, due to the use of an inhibitor which inhibits polymerization but does not affect the performance of the catalyst. Vinyl acetylene content of the effluent is generally less than bout 50 ppm in the single pass process which is carried out in a fixed bed reactor operating at elevated pressure. In an analogous process, from a crude isoprene feedstream containing up to about 1.0% by wt of isopropenyl acetylene and methyl acetylene, inter alia, an isoprene effluent is recovered having less than about 50 ppm alpha-acetylenes. The isoprene effluent, substantially free from poisons for a polyisoprene polymerization catalyst, contains essentially all the cyclopentadiene present in the feedstream. Cracking of impurities in the liquid phase minimizes the loss of this known cracking catalyst, permits it to have a much longer life, and, like the vapor phase catalytic cracking process using the same catalyst, produces at least 90% conversion of the acetylenes.

10 Claims, No Drawings

PROCESS FOR REMOVING α-ACETYLENES FROM DIOLEFINS

BACKGROUND OF THE INVENTION

The prior art is replete with processes for the purification of diolefin feed streams by removal of acetylenic impurities. These processes are generally characterized as belonging to one of four major categories, namely, (a) hydrogenation, (b) oxidation, (c) polymerization, and, (d) cracking, each generally being regarded as unrelated to the others.

A simple, physical distinction between the processes may be noted, in that only polymerization processes in which the acetylenic impurities are polymerized, are practiced in the liquid phase. For example, a polymerization catalyst useful in the liquid polymerization of alkyne impurities is disclosed in U.S. Pat. No. 3,105,858. In contrast, cracking processes in particular, are vapor phase processes carried out by contacting the impure feedstream with a cracking catalyst at relatively high temperature. Another noteworthy distinction is that, in general, cracking catalysts, polymerization catalysts, and hydrogenation or oxidation catalysts are each specific for the particular category of process in which each is most efficiently used.

A notable exception is the hydrogenation catalyst disclosed in the cracking process of U.S. Pat. No. 4,174,355 (hereafter the '355 patent) as a highly effective cracking catalyst. The effectiveness of this bifunctional catalyst as a cracking catalyst is thought to be predicated, at least in part upon the unusual operating characteristics of such a process, though the precise mechanism of how a typical hydrogenation catalyst also performs as a cracking catalyst is not known. For example, a vapor phase process provides higher diffusivities of the reactants, which decreases the mass transfer resistance. Since the difference in diffusivities between the liquid and vapor phases is several orders of magnitude, the latter being higher, a much longer residence time in the liquid phase would be indicated. Since the temperature at which the liquid phase process is to be carried out is unavoidably relatively high for a temperature-sensitive diolefin monomer, the liquid phase is contraindicated.

In the category of polymerization processes carried out in the liquid phase, the operating temperature is necessarily relatively low, usually lower than 150° F., yet the losses due to polymerization of the monomer being purified are still so high that such known processes are only of academic interest.

One of the earliest attempts to catalytically purify conjugated diolefins contaminated with acetylenic hydrocarbons is documented in U.S. Pat. No. 2,398,301 (4/1946) to Frevel, L. K. Soon thereafter, another catalytic process, stated to be a selective hydration process, was disclosed in U.S. Pat. No. 2,408,970 to Doumani et al for the removal of acetylenic impurities in hydrocarbon mixtures containing butadiene. At present, minor quantities of IPEA, and other $C_2$–$C_5$ acetylene are removed by selective hydrogenation of the acetylenes over a supported copper catalyst. Such processes are taught in U.S. Pat. No. 3,076,858 to Frevel et al; in U.S. Pat. No. 3,634,536 to Frevel L. K. and Dressley, L. J.; and, 3,751,508 to Fujiso et al, inter alia. Not long thereafter, an adsorption process carried out in the temperature range of 25° C.–175° C. was disclosed in U.S. Pat. No. 3,754,050 to Duyverman et al. Still more recently, U.S. Pat. No. 3,897,511 to Frevel, L. K. and Dressley, L. J., disclosed a catalytic process for removal of alpha-acetylenic impurities by their adsorption on a supported catalyst consisting essentially of a mixture of finely divided copper metal and a minor proportion of at least one polyvalent activator metal.

Polymer grade butadiene for the cis-polybutadiene polymerization system is obtained by purification of butadiene containing unacceptably high levels of apha-acetylenes such as vinyl acetylene and methyl acetylene. U.S. Pat. No. 3,897,511 teaches the selective chemisorption of alpha-acetylenes on copper catalysts activated with NiO, CoO, CrO or MnO. The activated copper catalyst is reduced with hydrogen prior to use. British Pat. No. 1,291,397 teaches a mixed CuO/Zno catalyst which can also be used for chemisorption of alpha-acetylenes.

The prior art is replete with a multiplicity of hydrogenation catalyst particularly suited for hydrogenation of acetylenic and other impurities in conjugated diolefin streams. A few of these catalysts are said to effectively lower the final acetylenic concentration of a feedstream from 1 percent to below 100 ppm without excessive conversion of the diene to a monoolefin or alkane, but the period of time over which the activity can be maintained is quite unpredictable. For one reason or another, some hydrogenation catalysts make for more successful hydrogenation processes than others, and the search for economically competitive processes, whether by hydrogenation or not, continues unremittingly.

As for a process other than selective hydrogenation for removal of acetylenic impurities from crude butadiene or isoprene, it will be evident that chemisorption of the impurities on active sites, for later removal of the impurities, necessitates impractically large quantities of adsorbent, even if the adsorbent has high surface area. Though neither selective hydrogenation nor chemisorption-desorption is as energy intensive as a vapor phase catalytic cracking process, none of the foregoing is economically as attractive as an energy non-intensive liquid phase process.

Relatively little interest has been directed to the conversion of alkynes by contact with base metal oxide catalysts without hydrogenation or hydration of the alkynes. Catalysts consisting of finely divided copper alone or mixed with an activator metal were known to be useful for removal of the alkynes by selectively decomposing or polymerizing these contaminants, but such a process, inter alia, was known to be subject to one or more disadvantages, as specifically stated in aforementioned U.S. Pat. No. 3,897,511, column 1, lines 26-43. As stated in the earlier Frevel U.S. Pat. No. 2,398,301, temperatures above 200° C. (392° F.) were indicated, 275° C. (527° F.) to 325° C. (617° F.) being preferred (page 2, right hand column, line 38). At these relatively higher temperatures, higher than 200°–260° F., not only alpha-acetylenes but also cyclopentadiene (hereafter "CPD" for brevity), is removed, and unavoidably, as evidenced by the exothermic reaction noted, a sufficiently large proportion of desirable diolefins are converted to mask the endothermic cracking of acetylenic impurities.

From a practical point of view, it is economically undesirable to hydrogenate a large feedstream of crude diolefin, no matter how selectively the hydrogenation can be effected, unless the hydrogenated feedstream is further distilled to produce an overhead with less than 50 ppm alpha-acetylenes, and, the impurities-rich bottoms are recycled to the hydrogenation unit for further hydrogenation. As already indicated hereinabove, it is also economically undesirable to catalytically crack the impurities in a large feedstream because of the energy required to vaporize the feedstream. Stated differently, there are many economically viable options for producing a diolefin feedstream with 1000 ppm or more alpha-acetylenic impurities, but to purify the feedstream still further, one is pincered between the high costs of purification due to losses caused by hydrogenating desired diolefin along with the impurities, and, the high cost of vapor phase catalytic cracking, because of high regeneration costs of catalyst and shortened catalyst life. The '355 process is the only vapor phase catalytic cracking process known to me which can purify a diolefin feedstream having about 1000 ppm alpha-acetylenic impurities more economically than prior art processes. Nevertheless, the high cost of vaporizing the feedstream still was an economic burden. We are unaware of any prior art which teaches an energy non-intensive process for the conversion of acetylenic impurities and their removal by the use of a supported copper oxide or silver oxide bifunctional catalyst, in the absence of hydrogen, in a liquid phase, effectively inhibited, predominantly catalytic cracking process.

SUMMARY OF THE INVENTION

A cyclic liquid phase, predominantly catalytic cracking process which is energy non-intensive has been discovered for the purification of crude conjugated diolefins, wherein acetylenic impurities are selectively removed without supplying hydrogen or oxygen to the reactor in which the process is carried out. The process provides the immediate benefits of not vaporizing the feedstream, and not utilizing hydrogen. Because this process can utilize an impure diolefin feed contaminated with more than 0.1 percent by weight (% by wt) alkynes, the process avoids unduly sacrificing diolefins in an additional distillation step to prepare a feed with less than 100 ppm alkyne impurities. The process makes it economically practical to treat and purify a suitably inhibited alkyne-contaminated conjugated diolefin having four to five straight-chain, or cyclic, carbon atoms, for use in a polymerization system, without debilitating conversion losses of valuable feed components; and, to treat a relatively refined diolefin feed if such is available, more effectively.

More particularly, a crude butadiene feedstream contaminated with up to about 0.1 percent of vinyl acetylene, ethylacetylene, and methylacetylene is inhibited with a nitro-aromatic inhibitor and contacted in the liquid phase at a pressure in the range from about 100 #/sq. in. gauge (psig) to about 1000 psig, with a supported cupric oxide or silver oxide catalyst, in a fixed bed reactor, in the absence of added hydrogen or oxygen. The alphaacetylenes are removed to a level less than about 100 ppm by weight of effluent, in a single pass without significant loss of diolefins. The energy required (BTU/# of feed) is about one-fifth (20%) of that required for an effective catalytic vapor phase cracking process such as that disclosed in the '355 patent. The feed may optionally be supplemented with a diluent liquid, including water and an inert hydrocarbon. The crude butadiene stream is contacted continuously with the fixed bed catalyst for about 72 hours to about 96 hours at a temperature in the range from about 200° F. to about 260 ° F. The feed is then discontinued, the reactor is regenerated in a known manner, and the reactor readied for reintroduction of the feed.

In an analogous process, a crude isoprene feedstream containing up to about 0.1 percent by weight of isopropenyl acetylene and other alpha-acetylenes, and more than about 0.5% by wt of CPD, is inhibited with a nitro-aromatic inhibitor, and contacted in the liquid phase at a pressure in the range from about 100 psig to about 1000 psig, with a supported cupric oxide or silver oxide catalyst, in a fixed bed reactor, in the absence of added hydrogen or oxygen. The energy required (BTU/# of feed) is about one third (33.33%) of that required in a vapor phase catalytic cracking process. The alpha-acetylenes in the reactor effluent are removed to a level less than about 100 ppm, and preferably less than 50 ppm by wt of effluent in a single pass, without substantially lessening the concentration of CPD. The crude isoprene feed may, optionally, be supplemented with diluent liquid including water and an inert hydrocarbon. The crude isoprene feed is contacted continuously with the fixed bed catalyst for about 72 hours to about 96 hours at a temperature in the range from about 200° F. to about 260 ° F. The feed is then discontinued, the catalyst is regenerated in a conventional manner, and the reactor readied for reintroduction of the feed, thus providing a cyclic, liquid phase process. Unconverted CPD in the effluent is removed by a subsequent fractional distillation step.

Whether the process of this invention is used to purify isoprene or butadiene by removal of contaminant acetylenic impurities, the purification is effected with less than 1% by wt loss of diolefins and essentially all CPD in the feed is unconverted. Quite surprisingly, conversion of acetylenic impurities is lower, and loss of diolefins fed is greater, when the supported cupric oxide or silver oxide catalyst is promoted with elements from Group VI and Group VIII of the Periodic Table.

Where a relatively refined feedstream of isoprene or butadiene is available, in which deleterious alpha-acetylene impurities are present in relatively low concentrations compared to their concentrations in a crude feedstream, the process of this invention makes it possible to remove these impurities with at least 90% conversion, to a low level sufficient to provide an effluent which can effect a polymerization catalyst savings of 50 percent or more, when the effluent, after a subsequent fractionation to remove unconverted CPD, is used in a synthetic natural rubber or polybutadiene polymerization system.

DETAILED DESCRIPTION OF PREFERRED EMBODIMENTS OF THE INVENTION

Crude butadiene, such as is typically used to furnish feedstock for a cis-polybutadiene catalytic polymerization system contains vinyl acetylene (hereafter "VA"), ethylacetylene (hereafter "EA"), and methylacetylene (hereafter "MA") in minor amounts which are deleterious to the system, and varying amounts of other impurities such as propadiene, lower paraffins, lower alkylenes and the like which are not harmful. Commercially available butadiene feed stock for cis-butadiene rubber production typically contains about 500 ppm alpha-acetylenes. This feed stock is obtained as an overhead from an extractive distillation column, and it is essential that the content of alpha-acetylenes be reduced to a much lower level, preferably at least 100 ppm, for good results in the cis-butadiene rubber polymerization process.

Isoprene, which is typically present in an amount less than about 50% by weight in a C$_5$ fraction from a naphtha cracking furnace, contains acetylenic IPEA, BY-2 and diolefinic CPD in minor amounts. In addition there may also be present minor amounts of (a) piperylenes, (b) other C$_5$ compounds such as 2-methyl butene-1, (hereafter "2-MB-1"), and 2-methyl butene-2, (hereafter "2-MB-2"), and, (c) other alpha-acetylenes such as trans-3-pente-1-yne (hereafter "t-PEY"), cis-3-penten-1-yne (hereafter "c-PEY"), and 1,4-Pentenyne (hereafter "1,4-PEY"). Pentenynes may be present in a concentration as high as about 0.1 percent.

The present process, in its most preferred embodiment, comprises contacting a feedstock of liquid conjugated diolefin contaminated with acetylenic impurities, with a solid Group I B metal oxide catalytic cracking catalyst at an elevated pressure in a reactor, at a temperature in the range from about 200° F. to about 260° F., and recovering an effluent in which alpha-acetylenic impurities have selectively been converted to compounds not harmful in a subsequent polymerization of the diolefin, but in which CPD, if present, is left unconverted. This process relies for its effectiveness upon the use of several critical process conditions. These conditions are as follows:(i) a cupric oxide cracking catalyst having more than 10% but less than 25% by weight cupric oxide in a fixed bed reactor, which cracking does away with a separate desorption ste, (ii) a narrow temperature range of from 200° to 260° F. in which the catalyst is surprisingly selective, (iii) use of a suitable inhibitor in the feed, (iv) no hydrogen or oxygen as feed to the reactor, (v) a liquid hourly space velocity (LHSV) of feed, in the range from about 1 to about 50 LHSV which results in (vi) essentially no conversion of CPD if it is present in the feed, (vii) at least 90% by weight conversion of the alpha-acetylenic impurities in the feed, and, (viii) loss of less than 1% by wt of diolefins fed to the reactor.

The presence of saturated hydrocarbons, and particularly butanes and pentanes in the feed, does not appear to influence the conversion of alph-acetylenes and the like, but appear to act only as diluents. Similarly, inert liquid diluents such as water may be present in the feed to the reactor without deleterious effect. No substantial improvement in conversion is observed when this process is carried out in the presence of a diluent, compared to a process under similar conditions, in the absence of a diluent; from an operating point of view it is preferred to keep diluents to a minimum. However, the commercial desirability of the process of this invention is based on energy savings, in that the feed is not vaporized, and that, despite the presence of relatively large proportions of diluent saturated hydrocarbons, the conversion of alpha-acetylenes is effected with surprising effectiveness and selectivity. The excellent selectivity of the process which limits the loss of diolefins in the feed to less than 1% by wt even at 90%, or better conversion, yet effect the conversion of alkynes, is corroborated by evidence that this process is not exothermic but endothermic. As is well known, an exothermic reaction which results in the removal of alkynes is indicative of a high level of conversion of diolefins, sufficient to mask the conversion of alkynes which is endothermic.

Only the oxides of copper and silver in the highest oxidation state, on a suitable catalyst support, will function in the conversion of alpha-acetylenes to compounds which will not adversely effect catalysts used in the polymerization of isoprene and butadiene. The oxides used are cupric oxide (CuO) and silver oxide (Ag$_2$O) supported on a catalyst support. Cupric oxide is most preferred for economical reasons. Unsupported cupric oxide catalyst is ineffective in this process, as is copper metal. The supported catalyst preferably contains from about 75 percent to about 90 percent by weight of a porous catalyst support and preferably from between about 80 percent to about 95 percent. A nonporous catalyst is effective for too short a period to be deemed economical in a commercial process. Any known catalyst support such as alumina, pumice, silicon carbide, zirconia, titania, alumina-silica, and the inorganic phosphates, silicated aluminates, borates and carbonates, stable under the reaction conditions, may be used, but those with relatively high (BET) surface area of at least 10 sq. meters/gm and high pore volume of at least 0.1 cc/gm are preferred. Most preferred is gamma-alumina having a surface area in excess of 100 m$^2$/gm, a pore volume in excess of 0.5 cc/gm and an average pore diameter greater than about 100 Å.

The supported catalyst may be prepared by any one of numerous methods of catalyst preparation known to those skilled in the art. The preferred manner of arriving at the oxides of the instant catalyst is by use of the water-soluble salts of copper and silver, from which the oxides are precipitated in situ. The supported catalyst's activity is enhanced by heating the catalyst at an elevated temperature. Preferably, the catalyst is heated at a temperature in the range from about 550° F. to about 800° F. for from about 2 hours to about 24 hours. If activity is insufficient, the catalyst can be heat-treated at even a higher temperature than 800° F. but well below a temperature deleterious to the catalyst, that is, a temperature at which the catalyst is deactivated, melted or decomposed.

A wide range of particle sizes for the supported oxide catalyst may be used, depending in part upon process conditions dictated by the choice of a fixed bed reactor. In this process, a fluidized bed of catalyst is of no particular advantage over a fixed bed. Accordingly relatively large particles of catalyst are preferred, the particular size being chosen with due regard for pressure drop and heat transfer considerations. A preferred particle size is in the range from about 25 U.S. Standard mesh to about ⅛ inch.

Excellent results are obtained whether the essential catalytic ingredient of the supported catalyst is cupric oxide or silver oxide. Since cupric oxide is more economical than silver oxide, particular reference herein is to cupric oxide, it being understood that silver oxide may be substituted for cuprix oxide, or a mixture of cupric oxide and silver oxide may be used.

To provide an economical process it is critical that the concentration of cupric oxide be in the range from 10 but less than 25 percent by weight of supported catalyst. Several suitable porous supported cupric oxide catalysts are presently commercially available. Of particular interest are Dow K catalyst obtained from Dow Chemical Co. and T-315, T-317, T-366, and T-1990 catalysts obtained from the Girdler Chemical Dept of Chemetron Corp. Most preferred is the T-1990 catalyst.

It is essential in this process to contact the supported cupric oxide catalyst with the impure diolefin feedstream in a narrow temperature range of about 200° F. to about 260° F., in which range the feed is in the liquid phase, the alkynes are converted, but CPD and other diolefins are not. The pressure at which the reaction is carried out is not critical, the conversion being substantially the same over a wide range from about 100 psig to about 1000 psig. It will thus be apparent that there is no economical advantage to carrying out the reaction at a pressure substantially greater than 1000 psig. Preferred operating pressures are in the range from about 150 psig to about 500 psig. No oxygenated organic compounds such as aldehydes and ketones are formed in the process. This evidence indicates that the process is not an oxidation process.

A relatively extended apparent contact time with the catalyst is required for effective removal of the alpha-acetylenic impurities. The apparent contact time is defined as the length of time in seconds which a unit volume of liquid, measured under the conditions of reaction, is in contact with the apparent unit volume of catalyst. The apparent contact time may be calculated, for instance, from the apparent volume of the catalyst bed, the average temperature and pressure of the reactor, and the flow rates in the reactor of the liquid feed components. The optimum contact time in the range from about 30 sec to about 100 secs, will depend on the diolefin being purified, the amount of diluent, and the concentration of impurities to be removed. Experimental results indicate that more than 1 g of alpha-acetylenes may be removed per g of supported catalyst. This amount removed is 920 times greater than the calculated theoretical amount of alpha-acetylene which may be removed by chemisorption alone. The catalyst is said to demonstrate a "turnover number" of 920. In general, the process of this liquid phase reaction allows the catalyst to demonstrate a turnover number in the range from about 400 to about 2000 which characterizes this liquid phase reaction as a predominantly catalytic cracking reaction. The vapor phase catalytic cracking reaction of the '355 patent demonstrates a turnover number in the range from about 100 to about 300, also indicating a predominantly cracking reaction. It is recognized that the generally long contact time of the liquid phase reaction is sufficient to permit polymerization of the alkynes, but it is self-evident that polymerization is contraindicated by the high turnover numbers, since the activity of the catalyst would be vitiated once the active sites were covered. The turnover number indicates a relatively small number of active sites available on the catalyst compared with the number of molecules of alpha-acetylenes converted.

After a period of many hours on stream, usually dictated by the level of alpha-acetylenes in the holding tank (also referred to as the "composite analysis"), or by the concentration of a particular impurity such as allyl acetylene in an isoprene feed, or vinyl acetylene in a butadiene feed, the feed is discontinued, as is any diluent liquid, if used. It is preferred to use a feed with as low a level of diluent as possible, and in the case of a relatively refined butadiene feed, this is relatively easily accomplished. In the case of an isoprene feed, even a relatively refined feed has a substantial concentration of diluent hydrocarbons. The reactor is then heated to a regeneration temperature in the range from about 600°-800° F. and the catalyst is regenerated with steam and a molecular oxygen containing gas, preferably air. There is no visual indication of any substantial reduction of the copper oxide prior to regeneration of the catalyst. When regeneration of the catalyst is complete, the reactor is readied for reintroduction of feed.

The precise period of onstream time in the catalytic conversion cycle of this vapor phase process will depend upon the size of the fixed bed, the level of contaminants in the feed, the flow rate through the reactor, the specific concentration of cupric oxide on the particular catalyst support used, the temperature at which the reactor is operated, and other factors. For example, it is preferred to use a diolefin feestream having about 1000 ppm alpha-acetylenes though higher concentrations up to about 5.0% by wt may be purified. It will be evident, upon calculation, that the optimum concentration of alkyne contaminants in the feed will be determined by the comparative cost of purification to a particular level by distillation, versus the pounds of feed purified per pound of catalyst, including the cost of regeneration of the catalyst.

In the examples hereinbelow, flow rates are measured as the liquid hourly space velocity, or LHSV, which is defined as the volumes of liquid component contacted at about 25° C. and at a pressure of about one atmosphere per volume of the solid catalyst particles per hour. All "percent" references are to percent by weight, unless otherwise specified.

EXAMPLE 1

A tubular reactor is packed with about 150 cc of 0.125 in. (nominal size) pellets of a catalyst comprising about 14 percent by weight cupric oxide on gamma alumina (T-1990 catalyst obtained from Girdler Chemicals Dept. of Chemetron Corp.) The reactor is packed by tapping it lightly to form a fixed bed. The reactor is heated and maintained at a temperature in the range from about 230° F. to about 250° F. and pressured with nitrogen gas to a pressure of about 325 psig. The catalyst has a surface area of about 200 sq meters/g, a pore volume of 0.54 cc/g, an average pore diameter of 133 Å and a bulk density of 35 lbs/ft$^3$.

The feed is a commercially available butadiene stream having less than 1000 ppm alpha-acetylenes. A typical such stream, which is also referred to as a "relatively refined" stream, has the following analysis:

| Component | Percent |
| --- | --- |
| n-butene | less than 1 |
| isobutene | less than 1 |
| butene-2 cis and trans | less than 1 |
| butadiene 1-3 | greater than 98 |
| butadiene 1-2 | less than 1 |
| propane and propylene | less than 0.1 |
| ethylacetylene | less than 100 ppm |
| vinylacetylene | 500-1000 ppm |
| methyl acetylene | less than 50 ppm |
| vinyl cyclohexene | less than 0.5 |

In a specific run, the tubular reactor is packed with T-1990 catalyst pellets, to form a fixed bed of about 100 cc. The reactor is then heated and maintained at a temperature of about 240° F. (near the center) and the reactor is pressurized with nitrogen to about 325 psig. Feed to the reactor is relatively refined butadiene (BN) crude having 556 ppm VA and 3 ppm MA. The results of the run are summarized in Table I hereinbelow. At the end of an 8 hour work period the reactor was idled or "held up" until the following working day by maintaining its temperature but discontinuing any feed to the reactor. The reactor is purged with nitrogen at the end of the day only to displace the feed remaining in the reactor. The nitrogen purge typically is completed within 10 minutes.

The feed contains about 500 ppm nitro-phenol inhibitor though substantially less provides effective inhibition. The feed also contains varying amounts of cyclohexene generally less than 1000 ppm. Both the inhibitor and the vinylcyclohexene pass through the reactor apparently unaffected, and without affecting the performance of the catalyst. The inhibitor is desirably recovered from the effluent and recycled. The cumulative catalyst life ("CCL" for brevity, in Table I) is stated as pounds (#) of butadiene (BN) feed per pound of catalyst (#BN/#cat). The composite analysis of the effluent in Table I is that of the accumulated effluent in a holding flask. I will be noted that the initial alkyne content of the effluent is high, apparently due to too low a temperature of the catalyst bed, with the result that the accumulated alkyne concentration as seen in the composite analysis starts out at a relatively high level and then drops off as the run continues, again increasing after continued operation of the reactor. The run was discontinued after 125 on-stream hours when the accumulated alkyne concentration reached 50 ppm. The loss of butadiene at the end of the run was less than 1% by wt of the butadiene in the feed.

The catalyst was regenerated by heating the bed to about 800° F. and contacting the heated bed with steam and air for about 5 hr at a steam flow rate of about 973 VVH (vapor velocity hours) and a maximum air flow rate of about 331 VVH. The bed is thereafter steamed for 1 hour with no additional air. The average inlet temperature is about 475° F. and the maximum bed temperature is about 845° F. After regeneration the catalyst's activity is restored essentially to its original activity level.

EXAMPLE 2

A relatively refined isoprene feed stream containing less than 1000 ppm isopropenylacetylene (IPEA) is treated in a manner analogous to that described in Example 1 hereinabove. In a specific run a tubular reactor is packed with 150 cc (79.6 g) of catalyst consisting essentially of about 14% CuO (T-1990 Girdler catalyst on a pororus gamma-alumina support). The reactor is heated and maintained at a temperature of about 220° F. and then pressured with nitrogen to about 150 psig. The

TABLE 1

| Onstr'm time(hr) | Temp °F. | Press psig | BN LHSV | CCL* #BN/#cat | Effluent anal VA ppm | MA** ppm | Composite anal VA ppm | MA** ppm |
|---|---|---|---|---|---|---|---|---|
| 0.5 | 220 | 325 | | | | | | |
| 2.0 | 235 | 325 | 8.4 | | 179 | 3 | | |
| 7.0 | 245 | 325 | 8.87 | | 30 | 3 | | |
| Holdup | | | | 81 | 30 | 3 | | |
| 15. | 250 | 330 | 17.1 | 194 | 10 | 3 | 17 | 3 |
| Holdup | | | | 263 | | | 13 | 3 |
| 22 | 235 | 326 | 17.45 | 340 | 9 | 3 | 12 | 3 |
| Holdup | | | | 410 | | | 12 | 3 |
| 29 | 240 | 318 | 15.07 | 479 | 7 | 3 | 11 | 3 |
| Holdup | | | | 539 | | | | |
| 37 | 240 | 283 | 14.61 | 622 | 12 | 3 | 11 | 3 |
| Holdup | | | | 644 | | | 11 | 3 |
| 42 | 235 | 308 | 15.32 | 708 | 19 | 3 | 12 | 3 |
| Holdup | | | | 764 | | | 13 | 3 |
| 47.5 | 240 | 313 | 15.82 | | 33 | 3 | 14 | 3 |
| Holdup | | | | 879 | | | 15 | 3 |
| 54 | 245 | 310 | 5.22 | 893 | 12 | 3 | 15 | 3 |
| Holdup | | | | 933 | | | 15 | 3 |
| 61 | 240 | 295 | 11.76 | 1005 | 22 | 3 | 17 | 3 |
| Holdup | | | | 1026 | | | 17 | 3 |
| 67 | 235 | 322 | 16.79 | 1106 | 76 | 3 | 18 | 3 |
| Holdup | | | | 1167 | | | 21 | 3 |
| 71.5 | 235 | 317 | 15.32 | 1206 | 83 | 3 | 23 | 3 |
| Holdup | | | | 1309 | | | 25 | 3 |
| 80 | 240 | 315 | 15.28 | 1366 | 20 | 3 | 25 | 3 |
| Holdup | | | | 1412 | | | 25 | 3 |
| 84.5 | 240 | 310 | 16.23 | 1453 | 51 | 3 | 26 | 3 |
| Holdup | | | | 1533 | | | 27 | 3 |
| 93 | 240 | 320 | 14.21 | 1609 | 65 | 3 | 28 | 3 |
| Holdup | | | | 1662 | | | 30 | 3 |
| 97.5 | 240 | 327 | 16.51 | 1701 | 50 | 3 | 31 | 3 |
| Holdup | | | | 1788 | | | 32 | 3 |
| 104 | 240 | 315 | 14.24 | 1825 | 60 | 3 | 32 | 3 |
| Holdup | | | | 1854 | | | 33 | 3 |
| 110 | 240 | 313 | 16.87 | 1936 | 82 | 3 | 35 | 3 |
| Holdup | | | | 1980 | | | 36 | 3 |
| 114.5 | 240 | 325 | 16.31 | 2022 | 193 | 3 | 39 | 3 |
| Holdup | | | | 2120 | | | 46 | 3 |
| 123 | 240 | 325 | 17.18 | 2206 | 159 | 3 | 50 | 3 |
| Holdup | | | | 2256 | | | 52 | 3 |

In the foregoing run which was made over a period of about three weeks, and spanned a period of about 123 on-stream hours, chromatographic analyses indicated that essentially no ketones, aldehydes or other oxygen-containing organic compounds are formed during the reaction. An examination of the catalyst, after the run was terminated, indicates no visual evidence of metallic copper being formed.

isoprene feedstream is also contaminated with about 114 ppm allylacetylene (AA), about 82 ppm cis-3-penten-1-yne (c-PEY), and about 0.21% cyclopentadiene (CPD). The concentration of isoprene (IP) in the feed is about 48.6%, the remainder mainly comprising other $C_5$ compounds such as 2-methyl butene-1, and 1-pentene (Pe-1). The feed is inhibited with a nitro-phenol inhibitor in an amount in the range from about 10 to about 100 ppm, and fed to the heated and pressurized reactor. As in the previous example, the reactor is held up at the end of each working day by discontinuing the feed but maintaining the temperature. The conc of diluent hydrocarbons is not set forth in the effluent analysis which was monitored for its AA concentration. The run was discontinued when the AA conc appeared to have reached 10 ppm. The results of the run are summarized in Table I hereinbelow. At the end of the run, the reactor was regenerated in a manner analogous to that described in Example 1 hereinabove.

TABLE II

| Time (hr) | Temp °F. | Press psig | IP LHSV | CCL* #IP/#cat | Effluent Analysis | | | | |
|---|---|---|---|---|---|---|---|---|---|
| | | | | | IP % | IPEA ppm | AA ppm | c-PEY ppm | CPD % |
| 1.5 | 215 | 145 | 4.38 | 5.4 | 47.81 | 6 | 1 | 1 | 1 |
| 7.0 | 220 | 155 | 5.11 | 39.2 | 47.8 | 1 | 1 | 1 | 0.2 |
| Holdup | | | | 41.7 | | | | | |
| 9.5 | 220 | 145 | 4.96 | 53.8 | 48.9 | 10 | 1 | 2 | 0.18 |
| 14.0 | 225 | 145 | 5.52 | 81.9 | 48.4 | 3 | 1 | 2 | 0.2 |
| Holdup | | | | 84.3 | | | | | |
| 15.5 | 220 | 145 | 4.51 | 89.9 | 48.7 | 20 | 1 | 4 | 0.21 |
| 19.5 | 220 | 145 | 5.21 | 115.4 | 47.7 | 19 | 1 | 6 | 0.2 |
| Holdup | | | | 118.0 | | | | | |
| 22.0 | 220 | 145 | 5.01 | 130.3 | 48.28 | 47 | 2 | 11 | 0.19 |
| 26.5 | 220 | 150 | 4.08 | 157.6 | 48.2 | 45 | 2 | 11 | 0.19 |
| Holdup | | | | 160.2 | | | | | |
| 29.0 | 220 | 164 | 4.91 | 172.2 | 46.85 | 139 | 10 | 27 | 0.2 |
| 33.5 | 220 | 164 | 5.76 | 200.3 | 48.5 | 100 | 6 | 24 | 0.18 |
| Holdup | | | | 203.0 | | | | | |
| 36.0 | 215 | 150 | 5.21 | 215.7 | 48.9 | 198 | 12 | 37 | 0.19 |
| 40.0 | 220 | 155 | 5.16 | 240.6 | 48.5 | 147 | 7 | 29 | 0.19 |
| Holdup | | | | 243.7 | | | | | |

Average LHSV = 19403/(40×97.5) = 4.98
Average Temp. = 219° F. taken near the center of the catalyst bed
Average Press. = 151 psig
Loss of isoprene in the run was less than 1% of the isoprene in the feed.

A comparison of the energy requirement for the vapor phase process of the '355 patent and the liquid phase process of this invention is set forth in Table III hereinbelow:

TABLE III

| Energy Requirements | | |
|---|---|---|
| | Vapor phase cat cracking | Liquid phase cat cracking |
| Isoprene | 504 BTU/# feed @ 400 | 160 BTU/# feed @ 5 |
| Butadiene | 635 BTU/# feed @ 500 VVH | 95 BTU/# feed @ 14 LHSV |

In the claims below, the term "consisting essentially of" is meant to include the essential catalytic ingredient, namely cupric oxide, or silver oxide, or mixtures thereof, but is not meant to exclude small amounts of other elements the presence of which may be incident to the quality, origin, or particular processing of raw materials used to manufacture the supported catalyst.

From the foregoing description of the manner in which the experimental runs were made, it will be apparent that there were no provisions for many process steps which would be engineered into a commercial unit.

I claim:

1. A process for removing alpha-acetylenes from a hydrocarbon liquid mixture comprising said alpha-acetylenes and a conjugated diolefin having four to five carbon atoms, which process comprises, (a) adding an inhibitor to said mixture in an amount sufficient to inhibit polymerization of said diolefin, (b) introducing said hydrocarbon liquid mixture and inhibitor, optionally with an inert diluent, to a fixed bed reactor without supplying hydrogen or oxygen thereto, (c) contacting said mixture at a temperature in the range from about 200° F. to about 260° F. with a solid porous supported catalyst selected from the group consisting essentially of supported cupric oxide, silver oxide, or mixtures thereof in the range from more than 10% but less than 25% by weight of said catalyst, at a liquid hourly space volocity (LHSV) in the range from about 1 to about 50, (d) cracking said alpha-acetylenes to non-oxygenated organic compounds so as to produce at least 90 percent conversion of said alpha-acetylenes in the effluent from said reactor, in which effluent cyclopentadiene, if present in the feed, is essentially unconverted, loss of diolefin is less than 1 percent by weight of the hydrocarbon feed, and (e) providing heat to said reactor so as to maintain said temperature range during said process.

2. The process of claim 1 wherein said alpha-acetylenes in said mixture are present in an amount up to about 5.0 percent by weight of said mixture, and said alpha-acetylenes in said effluent are present in an amount less than about 100 parts per million parts (ppm) by weight of said mixture.

3. The process of claim 2 wherein said porous catalyst support is gamma alumina and said alpha-acetylenes in said effluent are present in an amount less than about 50 parts per million parts (ppm) by weight of said mixture.

4. The process of claim 3 wherein said reactor is operated at a pressure in the range from about 100 psig (lbs/in$^2$gauge) to about 1000 psig.

5. The process of claim 4 wherein said conjugated diolefin in said hydrocarbon liquid mixture is isoprene and includes more than about 0.1 percent cyclopentadiene.

6. The process of claim 4 wherein said conjugated diolefin in said hydrocarbon liquid mixture is butadiene and includes vinyl acetylene, ethyl acetylene and methyl acetylene in a combined amount of less than 1% by weight of the butadiene.

7. The process of claim 5 wherein said alpha-acetylenes include up to about 0.1 percent isopropenyl acetylene.

8. The process of claim 4 including discontinuing introduction of said mixture to said reactor when said alpha-acetylene in said effluent are present in a preselected amount less than about 50 ppm, and regenerating said catalyst.

9. The process of claim 5 wherein said alpha-acetylenes in said hydrocarbon vapor mixture include pentenynes present in an amount up to about 0.1 percent, and said effluent is essentially free of said pentenynes.

10. The process of claim 4 wherein the catalyst demonstrates a turnover number in the range from about 400 to about 2000.

* * * * *